United States Patent [19]

Ishikawa et al.

[11] Patent Number: 5,376,686

[45] Date of Patent: Dec. 27, 1994

[54] BIGUANIDE DERIVATIVES, MANUFACTURING METHOD THEREOF, AND DISINFECTANTS CONTAINING THE DERIVATIVES

[75] Inventors: Hiroshi Ishikawa; Koichi Yasumura; Hidetsugu Tsubouchi, all of Otsu; Yukio Higuchi, Higashiosaka; Hisashi Tamaoka, Tokushima, all of Japan

[73] Assignee: Otsuka Pharmaceutical Co., Ltd.

[21] Appl. No.: 863,420

[22] Filed: Apr. 3, 1992

[30] Foreign Application Priority Data

Apr. 5, 1991 [JP] Japan .................................. 3-073202
Jun. 19, 1991 [JP] Japan .................................. 3-147644
Sep. 4, 1991 [JP] Japan .................................. 3-224306

[51] Int. Cl.$^5$ ..................... C07C 279/26; A01N 37/52
[52] U.S. Cl. ..................... 514/635; 564/234; 564/235
[58] Field of Search ..................... 564/234; 514/635

[56] References Cited

U.S. PATENT DOCUMENTS

| B 403,243 | 3/1976 | Diamond et al. | 260/293.79 |
| 2,455,896 | 12/1948 | Nagy | 260/565 |
| 2,510,081 | 6/1950 | Curd et al. | 260/565 |
| 2,544,827 | 3/1951 | Curd et al. | 260/565 |
| 3,152,181 | 10/1964 | Shapiro et al. | 260/564 |
| 3,183,230 | 5/1965 | Shapiro et al. | 260/244 |
| 3,366,650 | 1/1968 | Bernstein et al. | 260/343.7 |
| 3,879,541 | 4/1975 | Kabbe et al. | 424/326 |
| 3,891,705 | 6/1975 | Diamond et al. | 260/565 |
| 4,183,958 | 1/1980 | Brown et al. | 424/326 |
| 4,567,174 | 1/1986 | Edwards et al. | 514/210 |

FOREIGN PATENT DOCUMENTS

| 0763722 | 3/1971 | Belgium . |
| 0138304 | 4/1985 | European Pat. Off. . |
| 1015134 | 1/1949 | France . |
| 2100 | 1/1962 | France . |
| 2085665 | 12/1971 | France . |
| 2009738 | 9/1971 | Germany . |
| 577843 | 6/1946 | United Kingdom . |
| 1095902 | 12/1967 | United Kingdom . |

OTHER PUBLICATIONS

Warner et al. "Quantitative Structure–Activity Relationships for Biguanides" etc. *J. Med. Chem.* 1979, vol. 22, No. 4, 359–366.

Weinberg, "The Antimicrobial Activity of $N^1,N^5$-Substituted Biguanides", *Antibiotics and Chemotherapy* vol. XI, No. 9, p. 572 (Sep. 1961).

Neelakantan, L., "Preparation of Some 1,5-Diaryl Biguanides," J. Org. Chem., vol. 22, p. 1587 (Dec. 1957).

Weinberg, Eugene, "The Antimicrobial Activity of $N^1,N^5$-Substituted Biguanides," Antibiotics & Chemotherapy, vol. XI, No. 9, p. 572 (Sep. 1961).

Paul, S. P. et al., "Synthesis of Biguanides as Potential Hypoglycaemic Agents: Part IV—Structure–Activity Relationship," Indian J. Chem., vol. 1, p. 218 (May 1963).

*Primary Examiner*—Peter O'Sullivan
*Attorney, Agent, or Firm*—Sughrue, Mion, Zinn, Macpeak & Seas

[57] ABSTRACT

The invention presents a biguanide derivative or its salt expressed by a formula:

$$R^1-NH-\overset{NH}{\underset{\|}{C}}-NH-\overset{NH}{\underset{\|}{C}}-NH-R^2 \quad (1)$$

(where $R^1$ and $R^2$ are as defined in Specification), or formula:

$$R^3-NHCNHCNH-A-\!\!\left\langle\!\!\bigcirc\!\!\right\rangle\!\!-A-NHCNHCNH-R^3 \quad (2)$$

(where A and $R^3$ is as defined in specification). This biguanide derivative or its salt is preferably used as the effective amount of a disinfectant for humans, animals, medical appliances, etc.

7 Claims, No Drawings

BIGUANIDE DERIVATIVES, MANUFACTURING METHOD THEREOF, AND DISINFECTANTS CONTAINING THE DERIVATIVES

BACKGROUND OF THE INVENTION

The invention relates to novel biguanide derivatives used in disinfection of humans, animals, medical appliances, and others, a method of manufacturing the same, and disinfectants containing such derivatives.

It is known that various guanidine derivatives possess bactericidal actions, and biguanide derivatives of 1,4-dimethylene cyclohexane type are disclosed in the British Patent Specification No. 1,098,902.

SUMMARY OF THE INVENTION

It is a primary object of this invention to present novel biguanide derivatives or their salts possessing a higher activity than the conventional biguanide derivatives or their salts, and disinfectants containing such derivatives or their salts.

To achieve the above object, a monobiguanide derivative of the invention is a biguanide derivative or its salt, expressed by a general formula:

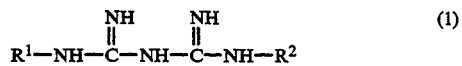

$$R^1-NH-\overset{NH}{\underset{\|}{C}}-NH-\overset{NH}{\underset{\|}{C}}-NH-R^2 \quad (1)$$

(where $R^1$ represents 3,4-dichlorobenzyl group, 4-chlorophenyl group, 3,4-dichlorophenyl group, benzyl group or 4-chlorobenzyl group, and $R^2$ represents octyl group, 3,4-dichlorobenzyl group, dodecyl group, decyl group, 3-trifluoromethylphenyl group, 4-bromophenyl group, 4-iodophenyl group, 2,4-dichlorophenyl group, 3,4-dichlorophenyl group, 2,3,4-trichlorophenyl group, 3,4-dimethylphenyl group, 3,4-methylenedioxyphenyl group, 4-t-butylphenyl group, 4-ethylthiophenyl group, 1,1,3,3-tetramethylbutyl group, hexyl group, 2-ethoxyethyl group, 2-(2-hydroxyethoxy)ethyl group, 3-diethylaminopropyl group, 3-(2-ethylhexyloxy)-propyl group, (3-isopropoxy)propyl group, (2-diethylamino)-ethyl group, (3-butyl)-propyl group, 3(di-n-butylamino)propyl group, cyclohexylmethyl group, 3-trifluoromethylphenyl group, 4-ethylthiophenyl group, 4-chlorobenzyl group, 2,4-dichlorobenzyl group, 4-acetylaminophenyl group, 3,4-methylenedioxyphenyl group, 3,4-methylenedioxybenzyl group, octyl group, 4-chlorobenzyl group, decyl group, dodecyl group, isobutyl group, 3,4-dichlorophenyl group, or hexyl group), and the derivative being $N^1$-(3,4-dichlorobenzyl)-$N^5$-octyl-biguanide, $N^1$-(4-chlorophenyl)-$N^5$-(3,4-dichlorobenzyl)-biguanide, $N^1$-(3,4-dichlorophenyl)-$N^5$-octyl-biguanide,
$N^1$-benzyl-$N^5$-dodecyl-biguanide,
$N^1$-benzyl-$N^5$-decyl-biguanide,
$N^1$-(3,4-dichlorobenzyl)-$N^5$-(3-trifluoromethylphenyl)-biguanide,
$N^1$-(3,4-dichlorobenzyl)-$N^5$-(4-bromophenyl)-biguanide,
$N^1$-(3,4-dichlorobenzyl)-$N^5$-(4-iodophenyl)-biguanide,
$N^1$-(3,4-dichlorobenzyl)-$N^5$-(2,4-dichlorophenyl)-biguanide,
$N^1$-(3,4-dichlorobenzyl)-$N^5$-(3,4-dichlorophenyl)-biguanide,
$N^1$-(3,4-dichlorobenzyl)-$N^5$-(2,3,4-trichlorophenyl)-biguanide,
$N^1$-(3,4-dichlorobenzyl)-$N^5$-(3,4-dimethylphenyl)-biguanide,
$N^1$-(3,4-dichlorobenzyl)-$N^5$-(3,4-methylenedioxyphenyl)-biguanide,
$N^1$-(3,4-dichlorobenzyl)-$N^5$-(4-t-butylphenyl)-biguanide,
$N^1$-(3,4-dichlorobenzyl)-$N^5$-(4-ethylthiophenyl)-biguanide,
$N^1$-(3,4-dichlorobenzyl)-$N^5$-(n-decyl)-biguanide,
$N^1$-(3,4-dichlorobenzyl)-$N^5$-(1,1,3,3-tetramethylbutyl)-biguanide,
$N^1$-(3,4-dichlorobenzyl)-$N^5$-hexyl-biguanide,
$N^1$-(3,4-dichlorobenzyl)-$N^5$-(2-ethoxyethyl)-biguanide,
$N^1$-(3,4-dichlorobenzyl)-$N^5$-[2-(2-hydroxyethoxy)ethyl]-biguanide,
$N^1$-(3,4-dichlorobenzyl)-$N^5$-(3-diethylaminopropyl)-biguanide,
$N^1$-(3,4-dichlorobenzyl)-$N^5$-[3-(2-ethylhexyloxy)-propyl]-biguanide,
$N^1$-(3,4-dichlorobenzyl)-$N^5$-[(3-isopropoxy)propyl]-biguanide,
$N^1$-(3,4-dichlorobenzyl)-$N^5$-[(2-diethylamino)-ethyl]-biguanide,
$N^1$-(3,4-dichlorobenzyl)-$N^5$-[(3-butyl)-propyl]-biguanide,
$N^1$-(3,4-dichlorobenzyl)-$N^5$-[3(di-n-butylamino)propyl]-biguanide,
$N^1$-(4-chlorophenyl)-$N^5$-cyclohexylmethyl-biguanide,
$N^1$-(4-chlorophenyl)-$N^5$-(3-trifluoromethylphenyl)-biguanide,
$N^1$-(4-chlorophenyl)-$N^5$-(4-ethylthiophenyl)-biguanide,
$N^1$-(4-chlorophenyl)-$N^5$-(4-chlorobenzyl)-biguanide,
$N^1$-(4-chlorophenyl)-$N^5$-(2,4-dichlorobenzyl)-biguanide,
$N^1$-(4-chlorophenyl)-$N^5$-(4-acetylaminophenyl)-biguanide,
$N^1$-(4-chlorophenyl)-$N^5$-(3,4-methylenedioxyphenyl)-biguanide,
$N^1$-(4-chlorophenyl)-$N^5$-(3,4-methyleneoxydibenzyl)-biguanide,
$N^1$-(4-chlorobenzyl)-$N^5$-octyl-biguanide,
$N^1$-(4-chlorobenzyl)-$N^5$-(4-chlorobenzyl)-biguanide,
$N^1$-(4-chlorobenzyl)-$N^5$-decyl-biguanide,
$N^1$-(4-chlorobenzyl)-$N^5$-dodecyl-biguanide,
$N^1$-(4-chlorobenzyl)-$N^5$-isobutyl-biguanide,
$N^1$-(4-chlorobenzyl)-$N^5$-(3,4-dichlorophenyl)-biguanide,
$N^1$-(3,4-dichlorophenyl)-$N^5$-(3,4-methylenedioxybenzyl)-biguanide,
$N^1$-(3,4-dichlorophenyl)-$N^5$-hexyl-biguanide,
$N^1$-(3,4-dichlorophenyl)-$N^5$-decyl-biguanide.

The biguanide derivative (1) or its salt of the invention possesses a higher bactericidal action or anti-bacterial action than a known biguanide. Therefore, the disinfectant of the invention contains the biguanide derivative expressed by Formula (1) or its salt as an active ingredient.

This invention also presents a novel bis-biguanide derivative or its salt expressed by a general formula (2):

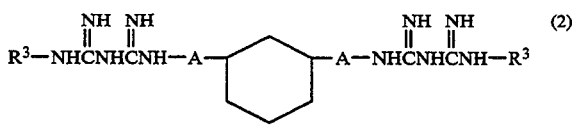

(where $R^3$ represents phenyl group which may posess one to three groups selected from a group consisting of halogen atom, lower alkyl group, halogen substituted lower alkyl group and lower alkylthio group as substituent; phenyl lower alkyl group which may possess a halogen atom as substituent on phenyl ring; or alkyl group, and A denotes a lower alkylene group).

The biguanide derivative (2) or its salt also possesses a high bactericidal action or antibacterial action same as the biguanide derivative (1). Therefore, the other disinfectant of this invention contains the bis-biguanide derivative expressed by Formula (2) or its salt as an active ingredient.

In the following explanation, the compound expressed by the general formula (1) is called as a monobiguanide derivative, and the compound expressed in Formula (2) is called a bis-biguanide derivative.

DETAILED DESCRIPTION OF THE INVENTION

The monobiguanide derivative expressed by Formula (1) or its salt of the invention is specifically represented in the Examples hereinafter.

The monobiguanide derivative (1) of the invention is a basic compound, and forms a corresponding acid-addition salt by reacting with an organic acid or an inorganic acid. Acids for forming such salt may include, for example, formic acid, acetic acid, lactic acid, butyric acid, isobutyric acid, α-mercaptopropionic acid, trifluoroacetic acid, malic acid, fumaric acid, succinic acid, succinic monoamide, glutamic acid, tartaric acid, oxalic acid, citric acid, glycolic acid, gluconic acid, saccharic acid, ascorbic acid, penicillin, benzoic acid, phthalic acid, salicylic acid, anthranilic acid, benzenesulfonic acid, p-toluenesulfonic acid, methansulfonic acid, hydrochloric acid, hydrobromic acid, sulfuric acid, phosphoric acid, nitric acid and carbonic acid, and are not particularly limited. Besides, the ratio of monobiguanide derivative and acid for forming acid-addition salt is not particularly limited, and salts of various ratios may be used such as 1:1, 1:2, or the like.

The acid-addition salt is manufactured in an ordinary salt forming method, such as direct mixing of acid and base, dissolving one or both in solvent such as water and mixing, and charging acid or base in solvent to dissolve and mix. After reaction, the obtained acid-addition salt is filtered if insoluble or hardly soluble in reaction medium, or recovered by evaporating the reaction medium if soluble in the reaction medium.

Such acid-addition salt itself exhibits a high bactericidal effect or antibacterial effect, and is also useful for refining or isolation of free base. Meanwhile, the acid-addition salt is preferred to be acceptable pharmaceutically.

The monobiguanide derivative (1) of this invention may also form a stable coordination compound with a metal salt. Such coordination compound also presents a bactericidal effect. The coordination compound is obtained by reaction of its derivative or its acid-adition salt with a specified quantity of metal salt, preferably a heavy metal salt such as V, Cr, Mn, Co, Ni, Cu, Zn, Pd, Re and Os.

Next is explained a manufacturing method of the monobiguanide derivative (1) of the invention.

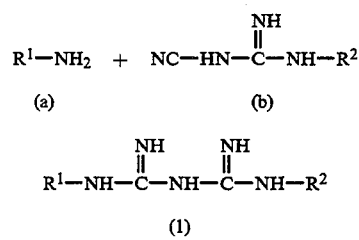

(where $R^1$ and $R^2$ are same as defined above.)

As shown in the reaction formula above, the monobiguanide derivative (1) of the invention is obtained by reaction of the amine expressed by Formula (a) with $N^1$-cyanoguanidine compound expressed by Formula (b). At this time, the amine (a) is used in about equimolecular amounts of the compound (b). The amine (a) may be used in a form of proper acid-addition salt such as hydrochloric acid salt.

The both components (a) and (b) are caused to react by heating in the presence or absence of inert solvent, such as 2-ethoxyethanol, 2-methoxyethanol and o-dichlorobenzene. If the product is an acid-addition salt, it may be changed into a form of free base by causing an alkali such as sodium hydroxide to act thereon, or may be changed into other acid-addition salt by ion exchange or other process.

The starting material expressed by Formula (b) may be manufactured, for example, in the following reaction formula.

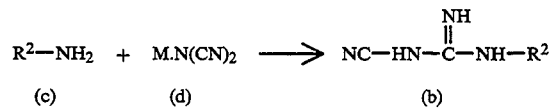

(where M represents an alkali metal, and $R^2$ is same as defined above.)

That is, the amine expressed by Formula (c) or its acid-addition salt (hydrochloride, etc.) is caused to react with the alkali metal salt (d) of dicyanamide (for example, sodium dicyanamide, potassium dicyanamide) in an inert solvent to obtain the material.

The monobiguanide derivative (1) of this invention may be also manufactured in the following reaction formula.

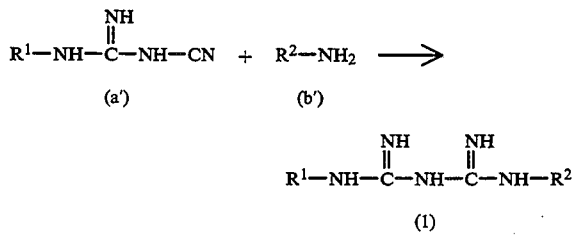

(where $R^1$ and $R^2$ represent the same as above.)

This reaction is performed nearly in the same condition as in the above reaction.

The bis-biguanide derivative (2) of this invention is described below. Examples of halogen atom represented by $R^3$ in Formula (3) may include chlorine, bromine, iodine and fluorine.

Examples of lower alkyl group include straight-chain or branched alkyl group having 1 to 6 carbon atoms, such as methyl, ethyl, n-propyl, isopropyl, n-butyl, isobutyl, tert-butyl, n-amyl, n-hexyl group, and the like.

Examples of halogen substituted lower alkyl group include halogen substitued lower alkyl group having 1 to 6 carbon atoms and replaced by 1 to 3 halogen atoms, such as monochloromethyl, monobromomethyl, monofluoromethyl, monoiodomethyl, dichloromethyl, dibromomethyl, difluoromethyl, diiodomethyl, trichloromethyl, tribromomethyl, trifluoromethyl, triiodomethyl, 3-chloropropyl, 3-fluoropropyl, 2,3-dichloropropyl, 3,3,3-trichloropropyl, 3-chloro-2-methylpropyl, 4-chlorobutyl, 4-fluorobutyl, 5-chloropentyl, 6-chlorohexyl, 6-fluorohexyl group, and the like.

Examples of lower alkylthio group include lower alkylthio group having straight-chain or branched alkyl moiety having 1 to 6 carbon atoms, such as methylthio, ethylthio, n-propylthio, isopropylthio, n-butylthio, isobutylthio, tert-butylthio, n-amylthio, n-hexylthio group, and the like.

Examples of phenyl lower alkyl group which may possess a halogen atom on a phenyl group as a substituent may include phenyl lower alkyl group possessing one to three phenyl groups which may have one to three halogen atoms, and having 1 to 6 carbon atoms in the alkyl moiety, such as benzyl, α-phenethyl, β-phenethyl, 3-phenylpropyl group, benzhydryl, trithyl, 4-chlorophenylmethyl, 3-chlorophenylmethyl, 2-chlorophenylmethyl, 3,4-dichlorophenylmethyl, 4-fluorophenylmethyl, 3,4-difluorophenylmethyl, 4-chlorophenylethyl, 3,4-dichlorophenylethyl group, and the like.

Examples of alkyl group used as subsituent $R^3$ are straight-chain or branched alkyl groups having 6 to 16 carbon atoms, specifically including n-hexyl, n-heptyl, n-octyl, n-nonyl, n-decyl, n-undecyl, n-tetradecyl, n-hexadecyl, 2-ethyl-1-hexyl, 2-ethyl-1-heptyl, 2-heptyl, 2-octyl, and 1,1,3,3-tetramethylbutyl group.

Examples of lower alkylene group include alkylene group having 1 to 6 carbon atoms, such as methylene, methylmethylene, ethylene, dimethylmethylene, trimethylene, 1-methyl-1-trimethyl, 2-methyltrimethylene, 2,2-dimethyltrimethylene, tetramethylene, pentamethylene, hexamethylene, and the like.

Practical examples of the bis-biguanide derivative (2) of the invention are shown in the table below.

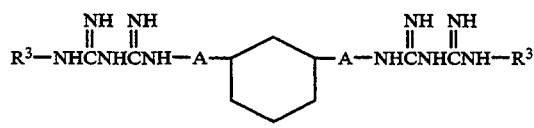

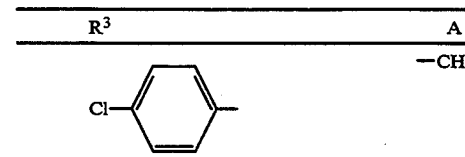

-continued

| R³ | A |
|---|---|
| H₇C₃—⟨phenyl⟩— | —CH₂CH₂— |
| Cl—⟨phenyl⟩— | " |
| ⟨phenyl⟩— | —CH₂— |
| ⟨phenyl⟩—(CH₂)₃ | " |
| CH₃(CH₂)₃CH(C₂H₅)CH₂— | " |
| Cl—⟨phenyl(Cl)⟩— | —(CH₂)₃— |
| H₃C—, (H₃C)₃C— | —CH₂—, " |

The bis-biguanide derivative (2) of this invention is a basic compound, and forms, same as the monobiguanide derivative (1), a corresponding acid-addition salt by reaction with various organic acids or inorganic acids.

The acid-addition salt of the bis-biguanide derivative (2) itself, as well as its derivative (2), exhibits a high bactericidal effect or antibacterial effect, and it is also useful for refining or isolation of free base. The acid-addition salt is preferred to be acceptable pharmaceutically. The bis-biguanide derivative (2) of the invention, same as the monobiguanide derivative (1), may also form a stable coordination compound with a metal salt, and such coordination compound also presents an excellent bactericidal effect.

The bis-biguanide derivative (2) of the invention is manufactured, for example, in the following reaction formula.

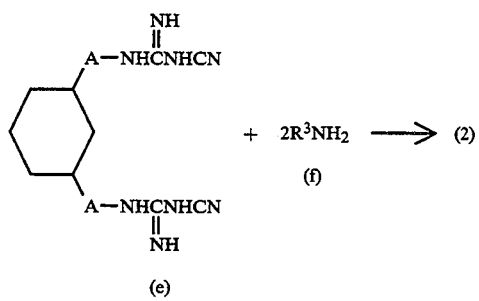

(where A and R³ represent same as defined above.)

As shown in the reaction formula above, the bis-biguanide derivative (2) of this invention is obtained by the reaction of 1,1'-[1,3-cyclohexanebis(alkylene)]-bis(3-cyanoguanidine) shown in Formula (e) with the amine shown in Formula (f). At this time, the amine (f) is used by about twice the tool equivalent of the compound (e). The amine (f) may be in a form of proper acid-addition salt such as hydrochloride.

The both components (e) and (f) are caused to react with each other by heating in the presence or absence of an inert solvent (e.g. 2-ethoxyethanol, 2-methoxyethanol, o-dichlorobenzene). If the reaction product is an acid-addition salt, it may be changed into a form of a free base by causing an alkali such as sodium hydroxide to act thereon, or changed into other acid-addition salt by ion exchange or other process.

The starting material expressed by Formula (e) may be manufactured, for example, in the following reaction formula.

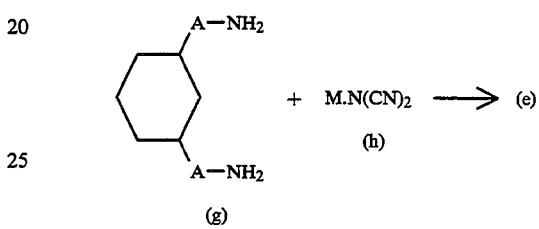

(where M denotes an alkali metal, and A is same as defined above.)

It is obtained, accordingly, by reaction of the diamine shown in Formula (g) or its acid-addition salt (hydrochloride, etc.) with the alkali metal salt (h) of dicyanamide (e.g. sodium dicyanamide, potassium dicyanamide) in an inert solvent.

The bis-biguanide derivative (2) of this invention may be also manufactured in the following reaction formula.

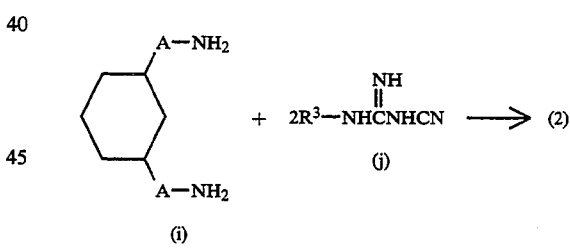

(where A and R³ represent the same as above.)

As shown in the above reaction formula, the bis-biguanide derivative (2) is obtained by the reaction between the diamine expressed by Formula (i) or its acid-addition salt (hydrochloride, etc.) and the cyanoguanidine compound expressed by Formula (j), in the presence or absence of an inert solvent. The reaction is conducted under heating. The cyanoguanidine compound (j) is used at a rate of about twice the mol equivalent of the diamine (i).

The biguanide derivatives (1), (2) of this invention and their salts possess higher antibacterial activities (bactericidal action or antibacterial action) as compared with the hitherto known biguanide derivatives, and some of them also possess antiviral activity. Furthermore, the biguanide derivatives (1), (2) of the invention and their salts possess a broad antibacterial spectrum, and are also excellent in rapidity of action, stability, safety and others, and their activities last for a long time. In addition, they are stimulation-free, odor-free, and soluble also in water. In particular, the compounds in Examples 1 to 4 mentioned below and their salts are particularly excellent in these features, and above all the compound of Example 1 and its salt are excellent in, including the above features, broad antibacterial spectrum, high short-time bactericidal activity, long-lasting drug effect, no problem in color, odor and taste, low toxicity, and the like. The salt of the compound of this invention is excellent in various points, including the above features, such as high solubility, low stimulation and toxicity, high stability, and the like.

Therefore, the biguanide derivatives (1), (2) of this invention and their salts are useful as active ingredient for disinfectants for humans, animals, and medical appliances. The disinfectant of this invention is used in a form of solution, dispersion or suspension by dissolving, dispersing or suspending a specified amount of the biguanide derivatives (1), (2) or their salts in water or organic solvent. Typical examples are eye-drop, nose-drop, gargle, detergent, cleaning agent, and other external application liquids. In these cases, the content of the biguanide derivatives (1), (2) or their salts may be usually about 0.01 to 20% by weight of the total amount.

Besides, the biguanide derivatives (1), (2) of this invention and their salts may be contained in various cosmetics, such as creams, lotions, powders, colors, makeups, toothpaste, shampoo, soap, depilatories, bleaches, hair-dyes, hair tonics, bath additives, manicure, antiperspiration agent, deodorant, aerosol cosmetics, and baby cosmetics, and the like.

Cosmetics are manufactured by dissolving, dispersing or suspending the specified amount of the biguanide derivatives (1), (2) or their salts, together with other ingredients, in water, other solvent, or various cosmetic bases. The content of the biguanide derivative (1), (2) or their salts in the cosmetic is usually about 0.001 to 1% by weight of the total amount.

EXAMPLES

Referring to examples, the biguanide derivative of this invention and the disinifectant containing the derivative are explained in detail below. It must be, however, noted that this invention is not limited to these examples.

EXAMPLE 1

Preparation of
$N^1$-(3,4-dichlorobenzyl)-$N^5$-octyl-biguanide hydrochloride

To 20 g of $N^1$-cyano-$N^3$-octyl-guanidine and 20.2 g of 3,4-dichlorobenzylamine hydrochloride, 200 ml of mesitylene was added, which was heated and refluxed for 1.5 hours. Returning to room temperature after reaction, mesitylene was removed. To the residue, 200 ml of 10% ethanol aqueous solution was added, which was heated, and stirred for 3 hours at room temperature to be solidified. It was filtered off, and washed with 10% ethanol solution, water and isopropylether in turn, and 28.1 g of rough product was obtained. It was recrystallized in ethyl acetate, and 22.1 g of the captioned compound was obtained.

White edged crystals mp. 177°~179° C.
Elemental analysis $C_{17}H_{28}Cl_3N_5$

|  | C | H | N |
|---|---|---|---|
| Calcd. | 49.95 | 6.90 | 17.13 |
| Found | 49.67 | 7.18 | 17.01 |

EXAMPLE 2

Preparation of
$N^1$-(4-chlorophenyl)-$N^5$-(3,4-dichlorobenzyl)-biguanide hydrochloride To 20 g of $N^1$-cyano-$N^3$-(3,4-dichlorobenzyl)-guanidine and 13.5 g of 4-chloroaniline hydrochloride, 200 ml of water was added, which was heated and refluxed for 2 hours. When cooled gradually after reaction, crystals was precipiated. After filtering the crystals, by drying the crystals obtained by heat treatment in 200 ml of ethyl acetate, 21.8 g of the captioned compound was obtained.

White edged crystals mp. 238°~240° C.
Elemental analysis $C_{15}H_{15}Cl_4N_5$

|  | C | H | N |
|---|---|---|---|
| Calcd. | 44.25 | 3.71 | 17.20 |
| Found | 44.19 | 3.66 | 17.17 |

EXAMPLE 3

Preparation of
$N^1$-(3,4-dichlorophenyl)-$N^5$-octyl-biguanide hydrochloride

In the same procedure as in Example 1 except that 3,4-dichlorobenzylamine hydrochloride was replaced by the equimolecular amount of 3,4-dichloroaniline hydrochloride, 28.2 g of the captioned compound was obtained.

White edged crystals mp. 176°~177° C.
Elemental analysis $C_{16}H_{26}Cl_3N_5$

|  | C | H | N |
|---|---|---|---|
| Calcd. | 48.68 | 6.64 | 17.74 |
| Found | 48.52 | 6.50 | 17.77 |

EXAMPLE 4

Preparation of $N^1$-benzyl-$N^5$-dodecyl-biguanide hydrochloride

To 20 g of $N^1$-cyano-$N^3$-benzyl-guanidine and 25.4 g of dodecylamine hydrochloride, 200 ml of mesitylene was added, which was heated and refluxed for 2 hours. After reaction, by the same operation as in Example 1, 23.7 g of the captioned compound was obtained.

White edged crystals mp. 135°~137° C.
Elemental analysis $C_{21}H_{38}ClN_5$

|  | C | H | N |
|---|---|---|---|
| Calcd. | 63.69 | 9.67 | 17.68 |
| Found | 63.47 | 9.41 | 17.73 |

EXAMPLE 5

Preparation of $N^1$-benzyl-$N^5$-decyl-biguanide hydrochloride

In the same manner as in Example 4 except that dodecylamine hydrochloride was replaced by the equimolecular amount of decylamine hydrochloride, 20.3 g of the captioned compound was obtained.

White edged crystals mp. 133°~135° C.
Elemental analysis $C_{19}H_{34}ClN_5$

|       | C     | H    | N     |
|-------|-------|------|-------|
| Calcd.| 62.02 | 9.31 | 19.03 |
| Found | 62.29 | 9.57 | 18.91 |

EXAMPLE 6

Preparation of $N^1$-(3,4-dichlorobenzyl)-$N^5$-(3-trifluoromethylphenyl)-biguanide hydrochloride In the same manner as in Example 2 except that 4-chloroaniline hydrochloride was replaced by the equimolecular amount of 3-trifluoromethylaniline hydrochloride, 23.2 g of the captioned compound was obtained.

White edged crystals mp. 185°~188° C.
Elemental analysis $C_{16}H_{15}Cl_3F_3N_5$

|       | C     | H    | N     |
|-------|-------|------|-------|
| Calcd.| 43.61 | 3.43 | 15.89 |
| Found | 43.57 | 3.24 | 16.10 |

EXAMPLE 7

Preparation of $N^1$-(3,4-dichlorobenzyl)-$N^5$-(4-bromophenyl)-biguanide hydrochloride In the same manner as in Example 2 except that 4-chloroaniline hydrochloride was replaced by the equimolecular amount of 4-bromoaniline hydrochloride, 21.6 g of the captioned compound was obtained.

White edged crystals mp. 223°~225° C.
Elemental analysis $C_{15}H_{15}BrCl_3N_5$

|       | C     | H    | N     |
|-------|-------|------|-------|
| Calcd.| 39.90 | 3.35 | 15.51 |
| Found | 40.34 | 3.16 | 15.82 |

EXAMPLE 8

Preparation of $N^1$-(3,4-dichlorobenzyl)-$N^5$-(4-iodophenyl)-biguanide hydrochloride In the same manner as in Example 2 except that 4-chloroaniline hydrochloride was replaced by the equimolecular amount of 4-iodoaniline hydrochloride, 22.6 g of the captioned compound was obtained.

White edged crystals mp. 215°~217° C.
Elemental analysis $C_{15}H_{15}Cl_3IN_5$

|       | C     | H    | N     |
|-------|-------|------|-------|
| Calcd.| 36.14 | 3.03 | 14.05 |
| Found | 36.25 | 2.80 | 14.21 |

EXAMPLE 9

Preparation of $N^1$-(3,4-dichlorobenzyl)-$N^5$-(2,4-dichlorophenyl)-biguanide hydrochloride In the same manner as in Example 2 except that 4-chloroaniline hydrochloride was replaced by the equimolecular amount of 2,4-dichloroaniline hydrochloride, 20.4 g of the captioned compound was obtained.

White edged crystals mp. 217°~220° C.
Elemental analysis $C_{15}H_{15}Cl_5N_5$

|       | C     | H    | N     |
|-------|-------|------|-------|
| Calcd.| 40.80 | 3.20 | 15.86 |
| Found | 41.25 | 2.93 | 15.79 |

EXAMPLE 10

Preparation of $N^1$-(3,4-dichlorobenzyl)-$N^5$-(3,4-dichlorophenyl)-biguanide hydrochloride In the same manner as in Example 2 except that 4-chloroaniline hydrochloride was replaced by the equimolecular amount of 3,4-dichloroaniline hydrochloride, 21.7 g of the captioned compound was obtained.

White edged crystals mp. 205°~208° C.
Elemental analysis $C_{15}H_{14}Cl_5N_5$

|       | C     | H    | N     |
|-------|-------|------|-------|
| Calcd.| 40.80 | 3.20 | 15.86 |
| Found | 41.03 | 2.94 | 15.94 |

EXAMPLE 11

Preparation of $N^1$-(3,4-dichlorobenzyl)-$N^5$-(2,3,4-trichlorophenyl)-biguanide hydrochloride In the same manner as in Example 2 except that 4-chloroaniline hydrochloride was replaced by the equimolecular amount of 2,3,4-trichloroaniline hydrochloride, 23.2 g of the captioned compound was obtained.

White edged crystals mp. 227°~228° C.
Elemental analysis $C_{15}H_{13}Cl_6N_5$

|       | C     | H    | N     |
|-------|-------|------|-------|
| Calcd.| 37.85 | 2.75 | 14.71 |
| Found | 38.09 | 2.55 | 14.81 |

EXAMPLE 12

Preparation of $N^1$-(3,4-dichlorobenzyl)-$N^5$-(3,4-dimethylphenyl)-biguanide hydrochloride In the same manner as in Example 2 except that 4-chloroaniline hydrochloride was replaced by the equimolecular amount of 3,4-dimethylaniline hydrochloride, 20.3 g of the captioned compound was obtained.

White edged crystals mp. 190°~191° C.

Elemental analysis $C_{17}H_{20}Cl_3N_5$

|  | C | H | N |
|---|---|---|---|
| Calcd. | 50.95 | 5.03 | 17.48 |
| Found | 50.66 | 4.78 | 17.56 |

EXAMPLE 13

Preparation of
$N^1$-(3,4-dichlorobenzyl)-$N^5$-(3,4-methylenedioxyphenyl)-biguanide hydrochloride In the same manner as in Example 2 except that 4-chloroaniline hydrochloride was replaced by the equimolecular amount of 3,4-methylenedioxyaniline hydrochloride, 25.7 g of the captioned compound was obtained.

White edged crystals mp. 204°~206° C.
Elemental analysis $C_{16}H_{16}Cl_3N_5O_2$

|  | C | H | N |
|---|---|---|---|
| Calcd. | 46.12 | 3.87 | 16.81 |
| Found | 45.83 | 3.69 | 16.97 |

EXAMPLE 14

Preparation of
$N^1$-(3,4-dichlorobenzyl)-$N^5$-(4-t-butylphenyl)-biguanide hydrochloride In the same manner as in Example 2 except that 4-chloroaniline hydrochloride was replaced by the equimolecular amount of 4-t-butylaniline hydrochloride, 22.5 g of the captioned compound was obtained.

White edged crystals mp. 228°~230° C.
Elemental analysis $C_{19}H_{24}Cl_3N_5$

|  | C | H | N |
|---|---|---|---|
| Calcd. | 53.22 | 5.64 | 16.33 |
| Found | 52.93 | 5.38 | 16.16 |

EXAMPLE 15

Preparation of
$N^1$-(3,4-dichlorobenzyl)-$N^5$-(4-ethylthiophenyl)-biguanide hydrochloride In the same manner as in Example 2 except that 4-chloroaniline hydrochloride was replaced by the equimolecular amount of 4-ethylthioaniline hydrochloride, 20.7 g of the captioned compound was obtained.

White edged crystals mp. 199°~200° C.
Elemental analysis $C_{17}H_{20}Cl_3N_5S$

|  | C | H | N |
|---|---|---|---|
| Calcd. | 47.18 | 4.66 | 16.18 |
| Found | 47.12 | 4.46 | 16.04 |

EXAMPLE 16

Preparation of
$N^1$-(3,4-dichlorobenzyl)-$N^5$-(n-decyl)-biguanide hydrochloride In the same manner as in Example 1 except that $N^1$-cyano-$N^3$-octyl-guanidine was replaced by the equimolecular amount of $N^1$-cyano-$N^3$-(n-decyl)-guanidine, 24.5 g of the captioned compound was obtained.

White edged crystals mp. 135°~137° C.
Elemental analysis $C_{19}H_{32}Cl_3N_5$

|  | C | H | N |
|---|---|---|---|
| Calcd. | 52.24 | 7.38 | 16.03 |
| Found | 52.08 | 7.12 | 16.31 |

EXAMPLE 17

Preparation of
$N^1$-(3,4-dichlorobenzyl)-$N^5$-(1,1,3,3-tetramethylbutyl)-biguanide hydrochloride In the same manner as in Example 1 except that $N^1$-cyano-$N^3$-oxtyl-guanidine was replaced by the equimolecular amount of $N^1$-cyano-$N^3$-(1,1,3,3-tetrabutyl)-guanidine, 23.1 g of the captioned compound was obtained.

White edged crystals mp. 196°~198° C.
Elemental analysis $C_{17}H_{28}Cl_3N_5$

|  | C | H | N |
|---|---|---|---|
| Calcd. | 49.95 | 6.90 | 17.13 |
| Found | 49.78 | 6.81 | 17.01 |

EXAMPLE 18

Preparation of
$N^1$-(3,4-dichlorobenzyl)-$N^5$-hexyl-biguanide hydrochloride

In the same manner as in Example 1 except that $N^1$-cyano-$N^3$-octyl-guanidine was replaced by the equimolecular amount of $N^1$-cyano-$N^3$-hexyl guanidine, 19.7 g of the captioned compound was obtained.

White edged crystals mp. 155°~157° C.
Elemental analysis $C_{15}H_{24}Cl_3N_5$

|  | C | H | N |
|---|---|---|---|
| Calcd. | 47.32 | 6.35 | 18.39 |
| Found | 47.21 | 6.17 | 18.50 |

EXAMPLE 19

$N^1$-(3,4-dichlorobenzyl)-$N^5$-(2-ethoxyethyl)-biguanide hydrochloride

In the same manner as in Example 1 except that $N^1$-cyano-$N^3$-octyl-guanidine was replaced by the equimolecular amount of $N^1$-cyano-$N^3$-(2-ethoxyethyl)-guanidine, 23.1 g of the captioned compound was obtained.

White edged crystals mp. 170°~173° C.
Elemental analysis $C_{13}H_{20}Cl_3N_5O$

|  | C | H | N |
|---|---|---|---|
| Calcd. | 42.35 | 5.47 | 18.99 |
| Found | 42.09 | 5.18 | 18.73 |

EXAMPLE 20

$N^1$-(3,4-dichlorobenzyl-$N^5$-[2-(2-hydroxyethoxy)ethyl]-biguanide hydrochloride In the same manner as in Example 1 except that $N^1$-cyano-$N^3$-octyl-guanidine was replaced by the equimolecular amount of $N^1$-cyano-$N^3$-[2-(2-hydroxyethoxy)ethyl]-guanidine, 21.5 g of the captioned compound was obtained.

White edged crystals mp. 140°~142° C.
Elemental analysis $C_{13}H_{20}Cl_3N_5O_2$

|  | C | H | N |
|---|---|---|---|
| Calcd. | 40.59 | 5.24 | 18.20 |
| Found | 40.30 | 5.01 | 18.03 |

EXAMPLE 21

Preparation of $N^1$-(3,4-dichlorobenzyl)-$N^5$-(3-diethylaminopropyl)-biguanide A rough product was obtained in the same manner as in Example 1 except that $N^1$-cyano-$N^3$-octyl-guanidine was replaced by the equimolecular amount of $N^1$-cyano-$N^3$-(3-diethylaminopropyl)-guanidine. The product was dissolved in 100 ml of methanol, and an equimolecular amount of 1N sodium hydroxide was added, which was concentrated at reduced pressure, and the residue was recrystallized in isopropanol, and 16.7 of the captioned compound was obtained.

White edged crystals mp. 156°~158° C.
Elemental analysis $C_{16}H_{26}Cl_2N_6$

|  | C | H | N |
|---|---|---|---|
| Calcd. | 51.48 | 7.02 | 22.51 |
| Found | 51.21 | 6.83 | 22.76 |

In the following Examples 22 to 26, using proper starting materials, the individual compounds were prepared in the same manner as in Example 1.

EXAMPLE 22

Preparation of $N^1$-(3,4-Dichlorobenzyl)-$N^5$-[3-(2-ethylhexyloxy)-propyl]-biguanide hydrochloride White edged crystals mp. 200°~203° C.
Elemental analysis $C_{20}H_{34}Cl_3N_5O$

|  | C | H | N |
|---|---|---|---|
| Calcd. | 51.45 | 7.34 | 15.00 |
| Found | 51.12 | 7.62 | 14.82 |

EXAMPLE 23

Preparation of $N^1$-(3,4-dichlorobenzyl)-$N^5$-[(3-isopropoxy)propyl]-biguanide hydrochloride White edged crystals mp. 158°~160° C.
Elemental analysis $C_{15}H_{24}Cl_3N_5O$

|  | C | H | N |
|---|---|---|---|
| Calcd. | 45.41 | 6.10 | 17.65 |
| Found | 45.17 | 6.02 | 17.53 |

EXAMPLE 24

Preparation of $N^1$-(3,4-dichlorobenzyl)-$N^5$-[(2-diethylamino)-ethyl]-biguanide White edged crystals mp. 137°~140° C.
Elemental analysis $C_{15}H_{24}Cl_2N_6$

|  | C | H | N |
|---|---|---|---|
| Calcd. | 50.14 | 6.73 | 23.39 |
| Found | 50.01 | 6.48 | 23.15 |

EXAMPLE 25

Preparation of $N^1$-(3,4-dichlorobenzyl)-$N^5$-[(3-butoxy)-propyl]-biguanide hydrochloride White edged crystals mp. 181°~184° C.
Elemental analysis $C_{16}H_{26}Cl_3N_5O$

|  | C | H | N |
|---|---|---|---|
| Calcd. | 46.78 | 6.38 | 17.05 |
| Found | 46.49 | 6.27 | 17.21 |

EXAMPLE 26

Preparation of $N^1$-(3,4-dichlorobenzyl)-$N^5$-[3-(di-n-butylamino)propyl]-biguanide dihydrochloride White edged crystals mp, 122°~124° C.
Elemental analysis $C_{20}H_{36}Cl_4N_6$

|  | C | H | N |
|---|---|---|---|
| Calcd. | 47.82 | 7.22 | 16.73 |
| Found | 47.72 | 7.01 | 16.65 |

EXAMPLE 27

Preparation of $N^1$-(4-chlorophenyl)-$N^5$-cyclohexylmethyl-biguanide hydrochloride In the same manner as in Example 2 except that $N^1$-cyano-$N^3$-(3,4-dichlorobenzyl)-guanidine was replaced by the equimolecular amount of $N^1$-cyano-$N^3$-cyclohexylmethyl-guanidine, 20.4 g of the captioned compound was obtained.

White edged crystals mp. 240°~241° C.
Elemental analysis $C_{15}H_{23}Cl_2N_5$

|  | C | H | N |
|---|---|---|---|
| Calcd. | 52.33 | 6.73 | 20.34 |
| Found | 52.24 | 6.61 | 20.48 |

EXAMPLE 28

Preparation of N$^1$-(4-chlorophenyl)-N$^5$-(3-trifluoromethylphenyl)-biguanide hydrochloride In the same manner as in Example 2 except that N$^1$-cyano-N$^3$-(3,4-dichlorobenzyl)-guanidine was replaced by the equimolecular amount of N$^1$-cyano-N$^3$-(3-trifluoromethylphenyl)-guanidine, 22.7 g of the captioned compound was obtained.

White edged crystals mp. 213°~215° C.
Elemental analysis C$_{15}$H$_{14}$Cl$_2$F$_3$N$_5$

|       | C     | H    | N     |
|-------|-------|------|-------|
| Calcd.| 45.93 | 3.60 | 17.86 |
| Found | 46.03 | 3.55 | 18.04 |

EXAMPLE 29

Preparation of N$^1$-(4-chlorophenyl)-N$^5$-(4-ethylthiophenyl)-biguanide hydrochloride In the same manner as in Example 2 except that N$^1$-cyano-N$^3$-(3,4-dichlorobenzyl)-guanidine was replaced by the equimolecular amount of N$^1$-cyano-N$^3$-(4-ethylthiophenyl)-guanidine, 20.76 g of the captioned compound was obtained.

White edged crystals mp. 243°~245° C.
Elemental analysis C$_{16}$H$_{19}$Cl$_2$N$_5$S

|       | C     | H    | N     |
|-------|-------|------|-------|
| Calcd.| 50.00 | 4.98 | 18.22 |
| Found | 50.04 | 4.82 | 18.10 |

EXAMPLE 30

Preparation of N$^1$-(4-chlorophenyl)-N$^5$-(4-chlorobenzyl)-biguanide hydrochloride In the same manner as in Example 2 except that N$^1$-cyano-N$^3$-(3,4-dichlorobenzyl)-guanidine was replaced by the equimolecular amount of N$^1$-cyano-N$^3$-(4-chlorobenzyl)-guanidine, 21.6 g of the captioned compound was obtained.

White edged crystals mp. 225°~227° C.
Elemental analysis C$_{15}$H$_{16}$Cl$_3$N$_5$

|       | C     | H    | N     |
|-------|-------|------|-------|
| Calcd.| 48.34 | 4.33 | 18.79 |
| Found | 48.32 | 4.19 | 18.86 |

EXAMPLE 31

Preparation of N$^1$-(4-chlorophenyl)-N$^5$-(2,4-dichlorobenzyl)-biguanide hydrochloride In the same manner as in Example 2 except that N$^1$-cyano-N$^3$-(3,4-dichlorobenzyl)-guanidine was replaced by the equimolecular amount of N$^1$-cyano-N$^3$-(2,4-dichlorobenzyl)-guanidine, 20.1 g of the captioned compound was obtained.

White edged crystals mp. 234°~236° C.
Elemental analysis C$_{15}$H$_{15}$Cl$_4$N$_5$

|       | C     | H    | N     |
|-------|-------|------|-------|
| Calcd.| 44.25 | 3.71 | 17.20 |
| Found | 44.42 | 3.50 | 16.95 |

EXAMPLE 32

Preparation of N$^1$-(4-chlorophenyl)-N$^5$-(4-acetylaminophenyl)-biguanide hydrochloride In the same manner as in Example 2 except that N$^1$-cyano-N$^3$-(3,4-dichlorobenzyl)-guanidine was replaced by the equimolecular amount of N$^1$-cyano-N$^3$-(4-acetylaminophenyl)-guanidine, 18.6 g of the captioned compound was obtained.

White edged crystals mp. 253°~255° C.
Elemental analysis C$_{16}$H$_{18}$Cl$_2$N$_6$O

|       | C     | H    | N     |
|-------|-------|------|-------|
| Calcd.| 50.40 | 4.76 | 22.04 |
| Found | 50.63 | 4.51 | 21.92 |

EXAMPLE 33

Preparation of N$^1$-(4-chlorophenyl)-N$^5$-(3,4-methylenedioxyphenyl)-biguanide hydrochloride In the same manner as in Example 2 except that N$^1$-cyano-N$^3$-(3,4-dichlorobenzyl)-guanidine was replaced by the equimolecular amount of N$^1$-cyano-N$^3$-(3,4-methylenedioxyphenyl)-guanidine, 19.7 g of the captioned compound was obtained.

White edged crystals mp. 237°~239° C.
Elemental analysis C$_{15}$H$_{15}$Cl$_2$N$_5$O$_2$

|       | C     | H    | N    |
|-------|-------|------|------|
| Calcd.| 48.93 | 4.11 | 8.69 |
| Found | 48.76 | 3.95 | 8.47 |

EXAMPLE 34

Preparation of N$^1$-(4-chlorophenyl)-N$^5$-(3,4-methylenedioxibenzyl)-biguanide hydrochloride In the same manner as in Example 2 except that N$^1$-cyano-N$^3$-(3,4-di chlorobenzyl)-guanidine was replaced by the equimolecular amount of N$^1$-cyano-N$^3$-(3,4-methylenedioxybenzyl)-guanidine, 22.4 g of the captioned compound was obtained.

White edged crystals mp. 231°~233° C.
Elemental analysis C$_{16}$H$_{17}$Cl$_2$N$_5$O$_2$

|       | C     | H    | N     |
|-------|-------|------|-------|
| Calcd.| 50.27 | 4.48 | 18.32 |
| Found | 50.44 | 4.29 | 18.31 |

EXAMPLE 35

Preparation of N$^1$-(4-chlorobenzyl)-N$^5$-octyl-biguanide hydrochloride

In the same manner as in Example 1 except that 3,4-dichlorobenzylamine hydrochloride was replaced by the equimolecular amount of 2,4-chlorobenzylamine hydrochloride, 21.3 g of the captioned compound was obtained.

White edged crystals mp. 156°~158° C.
Elemental analysis $C_{17}H_{29}Cl_2N_5$

|  | C | H | N |
|---|---|---|---|
| Calcd. | 54.54 | 7.81 | 18.71 |
| Found | 54.76 | 7.68 | 18.69 |

EXAMPLE 36

Preparation of $N^1$-(4-chlorobenzyl)-$N^5$-(4-chlorobenzyl)-biguanide hydrochloride Using 20.85 g of $N^1$-cyano-$N^5$-(4-chlorobenzyl)-guanidine and 17.8 g of 4-chlorobenzylamine hydrochloride, 21.4 g of the captioned compound was obtained by operating the same manner as in Example 1.

White edged crystals mp. 200°~202° C.
Elemental analysis $C_{16}H_{18}Cl_3N_5$

|  | C | H | N |
|---|---|---|---|
| Calcd. | 49.69 | 4.69 | 18.11 |
| Found | 49.62 | 4.61 | 18.37 |

EXAMPLE 37

Preparation of $N^1$-(4-chlorobenzyl)-$N^5$-decyl-biguanide hydrochloride

In the same manner as in Example 36 except that 4-chlorobenzylamine hydrochloride was replaced by the equimolecular amount of decylamine hydrochloride, 24.3 g of the captioned compound was obtained.

White edged crystals mp. 161°~163° C.
Elemental analysis $C_{19}H_{33}Cl_2N_5$

|  | C | H | N |
|---|---|---|---|
| Calcd. | 56.71 | 8.27 | 17.40 |
| Found | 56.60 | 8.12 | 17.63 |

EXAMPLE 38

Preparation of $N^1$-(4-chlorobenzyl)-$N^5$-dodecyl-biguanide hydrochloride

In the same manner as in Example 36 except that 4-chlorobenzylamine hydrochloride was replaced by the equimolecular amount of dodecylamine hydrochloride, 22.3 g of the captioned compound was obtained.

White edged crystals mp. 158°~160° C.
Elemental analysis $C_{21}H_{37}Cl_2N_5$

|  | C | H | N |
|---|---|---|---|
| Calcd. | 58.59 | 8.66 | 16.27 |
| Found | 58.41 | 8.53 | 16.55 |

EXAMPLE 39

Preparation of $N^1$-(4-chlorobenzyl)-$N^5$-isobutyl-biguanide hydrochloride

In the same manner as in Example 36 except that 4-chlorobenzylamine hydrochloride was replaced by the equimolecular amount of isobutylamine hydrochloride, 18.7 g of the captioned compound was obtained.

White edged crystals mp. 210°~221° C.
Elemental analysis $C_{13}H_{21}Cl_2N_5$

|  | C | H | N |
|---|---|---|---|
| Calcd. | 49.06 | 6.65 | 22.01 |
| Found | 48.87 | 6.52 | 22.23 |

EXAMPLE 40

Preparation of $N^1$-(4-chlorobenzyl)-$N^5$-(3,4-dichlorophenyl)-biguanide hydrochloride In the same manner as in Example 36 except that 4-chlorobenzylamine hydrochloride was replaced by the equimolecular amount of 3,4-dichloraniline hydrochloride, 21.7 g of the captioned compound was obtained.

White edged crystals mp. 183°~185° C.
Elemental analysis $C_{15}H_{15}Cl_4N_5$

|  | C | H | N |
|---|---|---|---|
| Calcd. | 44.25 | 3.71 | 17.20 |
| Found | 44.37 | 3.66 | 17.42 |

EXAMPLE 41

Preparation of $N^1$-(3,4-dichlorophenyl)-$N^5$-(3,4-methylenedioxybenzyl)-biguanide hydrochloride Using 21.5 g of $N^1$-cyano-$N^3$-(3,4-dichlorophenyl)-guanidine and 18.8 g of 3,4-methylenedioxybenzylamine hydrochloride, 27.3 g of the captioned compound was obtained by operating the same manner as in Example 1.

White edged crystals mp. 175°~177° C.
Elemental analysis $C_{16}H_{16}Cl_3N_5O_2$

|  | C | H | N |
|---|---|---|---|
| Calcd. | 46.12 | 3.87 | 16.81 |
| Found | 46.01 | 3.76 | 16.97 |

EXAMPLE 42

Preparation of $N^1$-(3,4-dichlorophenyl)-$N^5$-hexyl-biguanide hydrochloride

In the same manner as in Example 41 except that 3,4-methylenedioxybenzylamine hydrochloride was replaced by the equimolecular amount of hexylamine hydrochloride, 22.3 g of the captioned compound was obtained.

White edged crystals mp. 154°–156° C.
Elemental analysis $C_{14}H_{22}Cl_3N_5$

|  | C | H | N |
|---|---|---|---|
| Calcd. | 45.85 | 6.05 | 19.10 |
| Found | 45.66 | 6.17 | 19.03 |

EXAMPLE 43

Preparation of
$N^1$-(3,4-dichlorophenyl)-$N^5$-decyl-biguanide hydrochloride

In the same manner as in Example 41 except that 3,4-methylenedioxybenzylamine hydrochloride was replaced by the equimolecular amount of decylamine hydrochloride, 24.2 g of the captioned compound was obtained.

White edged crystals mp. 131°~133° C.
Elemental analysis $C_{18}H_{30}Cl_3N_5$

|  | C | H | N |
|---|---|---|---|
| Calcd. | 51.13 | 7.15 | 6.56 |
| Found | 51.02 | 7.32 | 16.37 |

EXAMPLE 44

Preparation of
$N^1$-(3,4-dichlorobenzyl)-$N^5$-octyl-biguanide lactate

Dissolving 20 g of $N^1$-(3,4-dichlorobenzyl)-$N^5$-octyl-biguanide hydrochloride in 200 ml of methanol, 24.5 ml of 5N NaOH was added, and the solvent was distilled away. The residual white solid was washed with water, suspended in 200 ml of water off, and 13 g of lactic acid was added, and dissolved by heating. Chilled in ice, precipitating crystals were filtered, and 12.14 g of the captioned compound was obtained.

White edged crystals mp. 45°~46° C.

EXAMPLE 45

Preparation of
$N^1$-(3,4-dichlorobenzyl)-$N^5$-octyl-biguanide glycolate

The captioned compound was obtained in the same manner as in Example 44 except that lactic acid was replaced by glycolic acid.

White edged crystals mp. 109°~110° C.

EXAMPLE 46

Preparation of
$N^1$-(3,4-dichlorobenzyl)-$N^5$-octyl-biguanide monomethanesulfonate The captioned compound was obtained in the smae manner as in Example 44 except that lactic acid was replaced by methanesulfonic acid.

White edged crystals mp. 174°~176° C.

EXAMPLE 47

Preparation of
$N^1$-(3,4-dichlorobenzyl)-$N^5$-octyl-biguanide hydrobromade

The captioned compound was obtained in the same manner as in Example 44 except that lactic acid was replaced by 47% hydrobromic acid.

White edged crystals mp. 120°~121° C.

EXAMPLE 48

Preparation of
$N^1$-(3,4-dichlorobenzyl)-$N^5$-octyl-biguanide phosphate

The captioned compound was obtained in the same manner as in Example 44 except that lactic acid was replaced by phosphoric acid.

White edged crystals mp. 96°~98° C.

EXAMPLE 49

Preparation of
$N^1$-(3,4-dichlorobenzyl)-$N^5$-octyl-biguanide dimethanesulfonate Dissolving 25 g of $N^1$-(3,4-dichlorobenzyl)-$N^5$-octyl-biguanide hydrochloride in 250 ml of methanol, 30.6 ml of 5N NaOH was added, and the solvent was distilled away. The residual white solid was washed with water, and dissolved in 500 ml of acetone, and 14.7 g of methanesulfonic acid was added. The precipitating crystals were filtered off, and by recrystallizing from ethanol-ether, 25.8 g of the captioned compound was obtained.

White edged crystals mp. 171°~172° C.
Elemental analysis $C_{17}H_{27}N_5Cl_2 \cdot 2CH_3SO_3H$

|  | C | H | N |
|---|---|---|---|
| Calcd. | 40.42 | 6.25 | 12.41 |
| Found | 40.40 | 6.55 | 12.31 |

REFERENCE EXAMPLE

Preparation of
$N^1$-(3,4-dichlorobenzyl)-$N^3$-cyanoguanidine

Putting 63.7 g (300 mM) of 3,4-dichlorobenzylamine hydrochloride and 30.9 g (1.1 eq.) of sodium dicyanamide in 950 ml (15 V) of acetonitrile, the mixture was heated and refluxed for 3.5 hours. Distilling away the solvent, 600 ml of water was added to the residue (white solid) to disperse and wash. Obtained crystals were filtered off, and dispersed and washed in 600 ml of dichloromethane. Since residue of amine was recognized, the crystals were dispersed and washed again in 600 ml of water and 500 ml of dichloromethane. Crystals were filtered off, and dried overnight at 60° C., and 57.7 g (78.9%) of the captioned compound was obtained.

White crystals mp. 173° C.
Elemental analysis $C_9H_8Cl_2N_4$

|  | C | H | N |
|---|---|---|---|
| Calcd. | 44.47 | 3.32 | 23.05 |
| Found | 44.32 | 3.08 | 23.30 |

EXAMPLE 50

Preparation of
$N^1$-(3,4-dichlorobenzyl)-$N^5$-octyl-biguanide dihydrochloride

Suspending 10.0 g (41.1 mM) of $N^1$-(3,4-dichlorobenzyl)-$N^3$-cyanoguanidine and 5.31 g (1.0 eq.) of n-octylamine in 100 ml of xylene, 3.5 ml (1.1 eq.) of concentrated hydrochloric acid was added and stirred for several minutes. The reaction was continued for 8 hours in reflux by using Dean-Stark trap. Distilling away the solvent, and by ethanol coboiling, xylene was removed. The residue was dissolved in 40 ml of 70% acetonitrile, and 6.8 ml (2.0 eq.) of concentrated hydrochloric acid was added. Further adding 90 ml of 70% acetonitrile, the mixture was recrystallized. Obtained cystals were filtered off, dried overnight at 60° C., and 14.3 g (78.2%) of white crystalline product was obtained. The obtained rough crystals were recrytallized twice with 70% acetonitrile (6 to 7 V), and 7.16 g (50.1%) of the captioned compound was obtained.

mp. 176°~178° C.

Elemental analysis $C_{17}H_{29}Cl_4N_5$

|  | C | H | N |
|---|---|---|---|
| Calcd. | 45.86 | 6.56 | 15.73 |
| Found | 45.54 | 6.66 | 15.79 |

Meanwhile, when the produced material (dihydrochloride) was recrystallized in a solvent of high water content (such as $CH_3CN$, ethanol), it was converted into the same monohydrochloride as obtained in Example 1.

| Prescription 1 of disinfectant | |
|---|---|
| Monobiguanide derivative of Example 1 | 5 g |
| Nonionic surface active agent (Polyoxyethylene phenylether) | 3.75 g |
| Distilled water for injection | proper |
| Whole volume | 100 ml |
| Prescription 2 of disinfectant | |
| Monobiguanide derivative of Example 1 | 0.5 g |
| Nonionic surface active agent (Polyoxyethylene phenylether) | 0.375 g |
| Ethanol | 83 ml |
| Distilled water for injection | proper |
| Whole volume | 100 ml |

Antibacterial activity test

In order to test the antibacterial action of the compounds obtained in the examples in various organisms, the minimum inhibitory concentration (MIC) was determined according to the standard method of Japan Society of Chemotherapy. The culture medium for sensitivity disc was used (Chemotherapy, vol. 29, No. 1, 76–79, 1981). As the control drug, gluconic chlorohexydine (tradename "Hibiten" commercially available from Sumitomo Pharmaceutical) was used and tested similarly. The results are shown in Table 1.

The inoculum size was adjusted to $1 \times 10^6$ cells/ml (0.07 to 0.16 at O.D. 600 nm).

TABLE 1

MIC µg/ml ($10^6$ cells/ml)

| Strain | Examples | | | | | | | | | |
|---|---|---|---|---|---|---|---|---|---|---|
|  | 1 | 2 | 3 | 4 | 5 | 6 | 7 | 8 | 9 | 10 |
| S. aureus FDA 209P | 1.56 | 1.56 | 3.13 | 1.56 | 0.78 | 3.13 | 1.56 | 1.56 | 1.56 | 0.78 |
| S. aureus MRSA 57 | 1.56 | 3.13 | 3.13 | 1.56 | 1.56 | 3.13 | 1.56 | 1.56 | 1.56 | 0.39 |
| E. coli NIHJ JC-2 | 100 | 12.5 | 6.25 | 100 | 50 | 12.5 | 6.25 | 12.5 | 25 | 6.25 |
| K. pneumoniae NCTC 9632 | — | — | — | — | — | — | — | — | — | — |
| S. marcescens IFO 12648 | 100 | 25 | 100 | 100 | 50 | 25 | 25 | 25 | 25 | 6.25 |
| P. aeruginosa ATCC 10145 | 100 | 25 | 100 | 100 |  | 100 | 50 | 100 | 100 | 25 |
| A. calcoaceticus Ac-54 | 25 | 12.5 | 12.5 | 100 | 25 | 12.5 | 6.25 | 12.5 | 6.25 | 3.13 |

| Strain | Examples | | | | | | | | | |
|---|---|---|---|---|---|---|---|---|---|---|
|  | 11 | 12 | 13 | 14 | 15 | 16 | 17 | 18 | 19 | 20 |
| S. aureus FDA 209P | 1.56 | 1.56 | 12.5 | 1.56 | 3.13 | 1.56 | 1.56 | 0.78 | 6.25 | 6.25 |
| S. aureus MRSA 57 | 0.78 | 1.56 | 12.5 | 1.56 | 3.13 | 1.56 | 1.56 | 0.78 | 6.25 | 6.25 |
| E. coli NIHJ JC-2 | 6.25 | 12.5 | 50 | 100 | 25 | 100 | 100 | 12.5 | 25 | 25 |
| K. pneumoniae NCTC 9632 | — | — | — | — | — | — | — | — | — | — |
| S. marcescens IFO 12648 | 12.5 | 25 | 50 | 50 | 100 | 100 | 100 | 12.5 | 50 | 50 |
| P. aeruginosa ATCC 10145 | 50 | 50 | 100 | 100 | 100 | 100 | 100 | 100 | 100 | 100 |
| A. calcoaceticus Ac-54 | 6.25 | 12.5 | 100 | 6.25 | 12.5 | 100 | 12.5 | 6.25 | 50 | 50 |

| Strain | Examples | | | | | | | | | |
|---|---|---|---|---|---|---|---|---|---|---|
|  | 21 | 22 | 23 | 24 | 25 | 26 | 27 | 28 | 29 | 30 |
| S. aureus FDA 209P | 12.5 | 1.56 | 3.13 | 6.25 | 1.56 | 6.25 | 6.25 | 6.25 | 6.25 | 3.13 |
| S. aureus MRSA 57 | 12.5 | 1.56 | 3.13 | 6.25 | 1.56 | 6.25 | 6.25 | 6.25 | 6.25 | 0.78 |
| E. coli NIHJ JC-2 | 100 | 100 | 50 | 100 | 25 | 50 | 25 | 25 | 12.5 | 12.5 |
| K. pneumoniae NCTC 9632 | — | — | — | — | — | 25 | — | — | — | — |
| S. marcescens IFO 12648 | 100 | 100 | 50 | 100 | 25 | 100 | 50 | 50 | 25 | 12.5 |
| P. aeruginosa ATCC 10145 | 100 | 100 | 100 | 100 | 100 | 100 | 100 | 100 | 100 | 25 |
| A. calcoaceticus Ac-54 | 100 | 100 | 50 | 100 | 25 | 100 | 12.5 | 12.5 | 12.5 | 6.25 |

| Strain | Examples | | | | | | | | | |
|---|---|---|---|---|---|---|---|---|---|---|
|  | 31 | 32 | 33 | 34 | 35 | 36 | 37 | 38 | 39 | 40 |
| S. aureus FDA 209P | 1.56 | 25 | 50 | 25 | 3.13 | 3.13 | 1.56 | 6.25 | 12.5 | 1.56 |
| S. aureus MRSA 57 | 0.78 | 12.5 | 50 | 25 | 3.13 | 3.13 | 1.56 | 6.25 | 12.5 | 1.56 |
| E. coli NIHJ JC-2 | 12.5 | 100 | 100 | 100 | 100 | 25 | 100 | 100 | 50 | 12.5 |
| K. pneumoniae NCTC 9632 | — | — | — | — | — | — | — | — | 50 | — |
| S. marcescens IFO 12648 | 12.5 | 100 | 100 | 100 | 100 | 25 | 100 | 100 | 100 | 12.5 |
| P. aeruginosa ATCC 10145 | 25 | 100 | 100 | 100 | 100 | 100 | 100 | 100 | 100 | 100 |
| A. calcoaceticus Ac-54 | 6.25 | 100 | 100 | 100 | 25 | 25 | 100 | 100 | 50 | 6.25 |

| Strain | Examples | | | | | | | Control agent |
|---|---|---|---|---|---|---|---|---|
|  | 41 | 42 | 43 | 44 | 45 | 46 | 49 |  |
| S. aureus FDA 209P | 12.5 | 3.13 | 6.25 | 1.56 | 1.56 | 1.56 | 1.56 | 1.56 |
| S. aureus MRSA 57 | 6.25 | 3.13 | 6.25 | 1.56 | 1.56 | 3.13 | 3.13 | 1.56 |
| E. coli NIHJ JC-2 | 25 | 12.5 | 100 | 100 | 100 | 100 | 100 | 1.56 |
| K. pneumoniae NCTC 9632 | — | — | 50 | — | — | — | — | — |
| S. marcescens IFO 12648 | 25 | 6.25 | 100 | 100 | 100 | 100 | 100 | 25 |

TABLE 1-continued

| P. aeruginosa ATCC 10145 | 100 | 6.25 | 100 | 100 | 100 | 100 | 100 | 100 |
|---|---|---|---|---|---|---|---|---|
| A. calcoaceticus Ac-54 | 25 | 12.5 | 100 | 25 | 25 | 25 | 50 | 12.5 |

Bactericidal activity test

As to the compounds obtained in Examples 1 and 2, the bactericidal activity at room temperature (25° C.) was measured by treating in a short time by reference to the phenol coefficient measurement method.

(1) Culture medium

For prior culture of test organism, Mueller Hinton Broth (DIFCD) was used. As growth culture medium of surviving cells in the test solution after bactericidal treatment, SCDLP culture medium inactivated by disinfectant was used ("Daigo" commercially available from Nippon Seiyaku).

(2) Test method

The compound obtained in each examples was dissolved in distilled water, and adjusted to a double concentration of the test concentration, and after aseptic filtering, the solution was diluted in steps of ½ in a range of Specified test concentration, and 50 μl was dispensed in 96-well microplate. On the other hand, the test organism undergoing the prior culture for 16 hours twice was adjusted to $10^8$ cells/ml with sterilized distilled water in order to eliminate the effects of culture medium (0.3 at O.D. 660 nm), and diluted to 1/100 with 5 ml or 10 ml of sterilized distilled water to obtain $10^6$ cells/ml, and into 50 μl of the test solution in the microplate, an equivalent 50 μl was injected and mixed. After the lapse of 1 minute and 3 minutes, 5 μl of the test solution was taken out from the microplate, and was suspended in 150 μl of inactivated culture medium, and was cultivated for 16 to 18 hours at 37° C. The survival of organisms in the test solution was judged by the turbidity, and the minimum bactericidal concentration in lapse of 1 minute and 3 minutes was determined. The result is shown in Table 2.

ature of 140° C., 51.3 g of 1,1'-[1,3-cyclohexanebis(methylene)]-bis(3-cyanoguanidine) was obtained.

Adding 5.52 g (0.02 mols) of this reaction product and 6.56 g (0.04 mols) of p-chloroaniline hydrochloride into β-oxyethylether (tradename: Cellosolve), by refluxing for 3 hours at 140° C. to react, 4.3 g of product was obtained. This product was recrystallized and refined in water and ethanol mixed solvent, and the captioned compound was obtained.

White edged crystals mp. 245°~248° C. NMR (CDCl$_3$+DMSO-d6) δ: 1.1~1.9 (m, 8H), 2.8~3.5 (m, 6H), 6.95 (bs), 7.37 (dd, 4H, J=9 Hz 7.90 (bs)

EXAMPLE 52

Preparation of 1,1'-[1,3-cyclohexanebis(methylene)]-bis[5-(4-iodophenyl)biguanide]dihydrochloride The captioned compound was obtained in the same manner as in Example 51 except that p-chloroaniline hydrochloride was replaced by the equimolecular amount of p-iodoaniline hydrochloride (Yield 5.1 g).

White edged crystals mp. 259°~261° C.

EXAMPLE 53

Preparation of 1,1'-[1,3-cyclohexanebis(methylene)]-bis[5-(4-bromophenyl)biguanide]dihydrochloride The captioned compound was obtained in the same manner as in Example 51 except that p-chloroaniline hydrochloride was replaced by the equimolecular amount of p-bromoaniline hydrochloride (Yield 4.7 g).

White edged crystals mp. 265°~267° C.

EXAMPLE 54

TABLE 2

| | Minimum Bactericidal Concentration μg/ml ($10^6$ cells/ml) | | | | | |
|---|---|---|---|---|---|---|
| | Example 1 | | Example 2 | | Control agent | |
| Strain | 1 min. | 3 min. | 1 min. | 3 min. | 1 min. | 3 min. |
| S. aureus FDA 209P | 12.5 | 3.13 | 500 | 100 | >1000 | 25 |
| S. aureus MRSA 57 | 6.25 | ≦1.56 | 200 | 25 | >1000 | 50 |
| E. coli NIHJ JC-2 | 3.13 | ≦1.56 | 25 | 6.25 | 12.5 | 6.25 |
| K. pneumoniae NCTC 9632 | 3.13 | 3.13 | 12.5 | 12.5 | 3.13 | ≦1.56 |
| S. marcescens IFO 12648 | 6.25 | ≦1.56 | 25 | 6.25 | 12.5 | 6.25 |
| A. calcoaceticus Ac-54 | 3.13 | 3.13 | 12.5 | 6.25 | 6.25 | 6.25 |
| P. aeruginosa ATCC 10145 | 3.13 | 3.13 | 12.5 | 6.25 | 12.5 | 6.25 |
| P. cepacia 2315-C0010 | 200 | 50 | 200 | 50 | >1000 | >1000 |

Thus, the monobiguanide derivative (1) of the invention or its salt possesses a high bactericidal action and antibacterial action, and hence it may be preferably used as the disinfectant for the human or animal skin or the like.

Next, the examples of bis-biguanide derivative (2) of this invention are explained.

EXAMPLE 51

Preparation of 1,1'-[1,3-cyclohexanebis(methylene)]-bis[5-(4-chlorophenyl)biguanide]dihydrochloride Refluxing 33 g (0.15 mols) of 1,3-di(aminomethyl) cyclohexane dihydrochloride and 26 g (0.3 mols) of dicyanamide sodium in buthanol for 12 hours at temper- Preparation of 1,1'-[1,3-cyclohexanebis(methylene)]-[5-(2,4-dichlorophenyl)biguanide]dihydrochloride The captioned compound was obtained in the same manner as in Example 51 except that p-chloroaniline hydrochloride was replaced by the equimolecular amount of 2,4-dichloroaniline hydrochloride (Yield 5.7 g).

White edged crystals mp. 261°~265° C.

EXAMPLE 55

Preparation of 1,1'-[1,3-cyclohexanebis(methylene)]-[5-(2,4-difluorophenyl)biguanide]dihydrochloride The captioned compound was obtained in the same manner as in Example 51 except that p-chloroaniline hydrochloride was replaced by the equimolecular amount of 2,4-difluoroaniline hydrochloride (Yield 4.1 g).

White edged crystals mp. 212°~215° C.

EXAMPLE 56

Preparation of 1,1'-[1,3-cyclohexanebis(methylene)]-[5-(4-t-butylphenyl)biguanide]dihydrochloride The captioned compound was obtained in the same manner as in Example 51 except that p-chloroaniline hydrochloride was replaced by the equimolecular amount of p-t-butylaniline hydrochloride (Yield 3.6 g).

White edged crystals mp. 194°~197° C.

EXAMPLE 57

Preparation of 1,1'-[1,3-cyclohexanebis(methylene)]-[5-(3,4-dimethylphenyl)biguanide]dihydrochloride The captioned compound was obtained in the same manner as in Example 51 except that p-chloroaniline hydrochloride was replaced by the equimolecular amount of 3,4-dimethylaniline hydrochloride (Yield 3.8 g).

Pale yellow edged crystals mp. 162°~166° C.

EXAMPLE 58

Preparation of 1,1'-[1,3-cyclohexanebis(methylene)]-[5-(4-ethylthiophenyl)biguanide]dihydrochloride The captioned compound was obtained in the same manner as in Example 51 except that p-chloroaniline hydrochloride was replaced by the equimolecular amount of p-ethylthioaniline hydrochloride (Yield 5.4 g).

mp. 110°~113° C.

EXAMPLE 59

Preparation of 1,1'-[1,3-cyclohexanebis(methylene)]-[5-(3-trifluoromethylphenyl)biguanide]dihydrochloride The captioned compound was obtained in the same manner as in Example 51 except that p-chloroaniline hydrochloride was replaced by the equimolecular amount of p-trifluoromethylaniline hydrochloride (Yield 2.5 g).

White edged crystals mp. 240°~242° C.

EXAMPLE 60

Preparation of 1,1'-[1,3-cyclohexanebis(methylene)]-[5-(2-ethylhexyl)biguanide]dihydrochloride The captioned compound was obtained in the same manner as in Example 51 except that p-chloroaniline hydrochloride was replaced by the equimolecular amount of p-(2-ethylhexyl)aniline hydrochloride (Yield 4.6 g).

White edged crystals mp. 105°~107° C.

EXAMPLE 61

Preparation of 1,1'-[1,3-cyclohexanebis(methylene)]-[5-(3,4-dichlorobenzyl)biguanide]dihydrochloride The captioned compound was obtained in the same manner as in Example 51 except that p-chloroaniline hydrochloride was replaced by the equimolecular amount of 3,4-dichlorobenzylamine hydrochloride (Yield 5.3 g).

White edged crystals mp. 231°~233° C.

EXAMPLE 62

Preparation of 1,1'-[1,3-cyclohexanebis(methylene)]-[5-(3,4-dichlorophenyl)biguanide]dihydrochloride The captioned compound was obtained in the same manner as in Example 51 except that p-chloroaniline hydrochloride was replaced by the equimolecular amount of 3,4-dichloroaniline hydrochloride (Yield 3.7 g).

White edged crystals mp. 259°~261° C.

EXAMPLE 63

Preparation of 1,1'-[1,3-cyclohexanebis(methylene)]-[5-benzylbiguanide]dihydrochloride The captioned compound was obtained in the same manner as in Example 51 except that p-chloroaniline hydrochloride was replaced by the equimolecular amount of benzylamine hydrochloride (yield 5.9 g).

White edged crystals mp. 208°~211° C.

EXAMPLE 64

Preparation of 1,1-'[1,3-cyclohexanebis(methylene)]-[5-(4-chlorobenzyl)biguanide]dihydrochloride The captioned compound was obtained in the same manner as in Example 51 except that p-chloroaniline hydrochloride was replaced by the equimolecular amount of 4-chlorobenzylamine hydrochloride (Yield 4.4 g).

White edged crystals mp. 204°~207° C.

| Prescription 3 of disinfectant | |
| --- | --- |
| Gluconic acid salt of Example 51 | 5 g |
| Nonionic surface active agent (Polyoxyethylene phenylether) | 3.75 g |
| Distilled water for injection | proper |
| Whole volume | 100 ml |
| Prescription 4 of disinfectant | |
| Gluconic acid salt of Example 51 | 0.5 g |
| Nonionic surface active agent (Polyoxyethylene phenylether) | 0.375 g |
| Ethanol | 8.3 ml |
| Distilled water for injection | proper |
| Whole volume | 100 ml |

Antibacterial activity test

To investigate the antibacterial actions of the compounds obtained in Examples 51 to 64, the minimum inhibitory concentration (MIC) was determined by employing the standard method of Japan Society of Chemotherapysame as mentioned above. The results are shown in Table 3.

TABLE 3

| | MIC μg/ml ($10^6$ cells/ml) | | | | | | |
|---|---|---|---|---|---|---|---|
| | Examples | | | | | | |
| Strain | 51 | 52 | 53 | 54 | 55 | 56 | 57 |
| S. aureus FDA 209P | 0.39 | 0.39 | 0.39 | 0.78 | 3.13 | 3.13 | 1.56 |
| S. epidermidis ATCC 12228 | 0.39 | 0.39 | 0.39 | 0.39 | 3.13 | 1.56 | 1.56 |
| E. coli NIHJ JC-2 | 3.13 | 6.25 | 3.13 | 6.25 | 25 | 25 | 12.5 |
| S. typhi NCTC 8393 | 1.56 | 6.25 | 3.13 | 6.25 | 6.25 | 12.5 | 6.25 |
| S. marcescens IFO 12648 | 6.25 | 12.5 | 6.25 | 50 | 50 | 50 | 50 |
| P. aeruginosa ATCC 10145 | 12.5 | 100 | 25 | 50 | 100 | >100 | 100 |
| C. alficans IFO 1385 | 3.13 | 6.25 | 6.25 | 6.25 | 25 | 50 | 100 |
| A. fumigatus IFM 4942 | 125 | 250 | 125 | 250 | 400 | >400 | >400 |

| | Examples | | | | | Control agent |
|---|---|---|---|---|---|---|
| Strain | 59 | 61 | 62 | 63 | 64 | |
| S. aureus FDA 209P | 1.56 | 3.13 | 0.78 | 3.13 | 1.56 | 1.56 |
| S. epidermidis ATCC 12228 | 1.56 | 1.56 | 0.39 | 1.56 | 1.56 | 0.78 |
| E. coli NIHJ JC-2 | 12.5 | 12.5 | 6.25 | 25 | 25 | 1.56 |
| S. typhi NCTC 8393 | 6.25 | 12.5 | 6.25 | 25 | 6.25 | 1.56 |
| S. marcescens IFO 12648 | 25 | 50 | 25 | 50 | 25 | 25 |
| P. aeruginosa ATCC 10145 | >100 | >100 | 100 | >100 | >100 | >100 |
| C. alficans IFO 1385 | 100 | 100 | 6.25 | 100 | 100 | 5 |
| A. fumigatus IFM 4942 | >200 | >200 | 125 | >200 | >200 | >200 |

What is claimed is:

1. A biguanide derivative or its salt selected from:
   $N^1$-(3,4-dichlorobenzyl)-$N^5$-octyl-biguanide or its salt,
   $N^1$-(3,4-dichlorophenyl)-$N^5$-octyl-biguanide or its salt,
   $N^1$-(3,4-dichlorobenzyl)-$N^5$-(n-decyl)-biguanide or its salt,
   $N^1$-(3,4-dichlorobenzyl)-$N^5$-(1,1,3,3-tetramethylbutyl)-biguanide or its salt,
   $N^1$-(3,4-dichlorobenzyl)-$N^5$-hexyl-biguanide or its salt,
   $N^1$-(3,4-dichlorobenzyl)-$N^5$-(2-ethoxyethyl-(biguanide or its salt,
   $N^1$-(3,4-dichlorobenzyl)-$N^5$-[2-(2-hydroxyethoxy)ethyl]-biguanide or its salt,
   $N^1$-(3,4-dichlorobenzyl)-$N^5$-(3-diethylaminopropyl)-biguanide or its salt,
   $N^1$-(3,4-dichlorobenzyl)-$N^5$-[(2-diethylamino)-ethyl]-biguanide or its salt,
   $N^1$-(3,4-dichlorobenzyl)-$N^5$-[3-(di-n-butylamino)-propyl]-biguanide or its salt,
   $N^1$-(3,4-dichlorophenyl)-$N^5$-hexyl-biguanide or its salt, and
   $N^1$-(3,4-dichlorophenyl)-$N^5$-decyl-biguanide or its salt.

2. A biguanide derivative or its salt selected from:
   $N^1$-(3,4-dichlorobenzyl)-$N^5$-octyl-biguanide or its salt, and
   $N^1$-(3,4-dichlorophenyl)-$N^5$-octyl-biguanide or its salt.

3. $N^1$-(3,4-Dichlorobenzyl)-$N^5$-octyl-biguanide or its salt.

4. The biguanide or its salt of claim 3, selected from:
   $N^1$-(3,4-dichlorobenzyl)-$N^5$-octyl-biguanide hydrochloride,
   $N^1$-(3,4-dichlorobenzyl)-$N^5$-octyl-biguanide lactate,
   $N^1$-(3,4-dichlorobenzyl)-$N^5$-octyl-biguanide gluconate,
   $N^1$-(3,4-dichlorobenzyl)-$N^5$-octyl-biguanide monomethaesulfonate,
   $N^1$-(3,4-dichlorobenzyl)-$N^5$-octyl-biguanide hydrobromide,
   $N^1$-(3,4-dichlorobenzyl)-$N^5$-octyl-biguanide phosphate,
   $N^1$-(3,4-dichlorobenzyl)-$N^5$-octyl-biguanide dimethanesulfonate, and
   $N^1$-(3,4-dichlorobenzyl)-$N^5$-octyl-biguanide dihydrochloride.

5. A disinfectant composition comprising an effective amount of the biguanide derivative or its salt of claim 1, and its carrier.

6. A disinfectant composition comprising an effective amount of the biguanide derivative or its salt of claim 2, and its carrier.

7. A disinfectant composition comprising an effective amount of the biguanide or its salt of claim 3, and its carrier.

* * * * *